US008858653B2

(12) United States Patent
Schettiger et al.

(10) Patent No.: US 8,858,653 B2
(45) Date of Patent: Oct. 14, 2014

(54) COLOR INTENSIFICATION BY POLYQUATERNIUM

(71) Applicant: Henkel AG & Co. KGaA, Düsseldorf (DE)

(72) Inventors: Norbert Schettiger, Hilden (DE); Frank Janssen, Köln (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/268,540

(22) Filed: May 2, 2014

(65) Prior Publication Data

US 2014/0237734 A1 Aug. 28, 2014

Related U.S. Application Data

(63) Continuation of application No. PCT/EP2012/069979, filed on Oct. 9, 2012.

(30) Foreign Application Priority Data

Nov. 4, 2011 (DE) .......................... 10 2011 085 754

(51) Int. Cl.
*A61Q 5/10* (2006.01)
*A61K 8/81* (2006.01)

(52) U.S. Cl.
CPC ................ *A61K 8/8152* (2013.01); *A61Q 5/10* (2013.01)
USPC ............................ 8/405; 8/406; 8/552; 8/558

(58) Field of Classification Search
CPC ................................. A61Q 5/10; A61K 8/8152
USPC ........................................ 8/405, 406, 552, 558
See application file for complete search history.

(56) References Cited

U.S. PATENT DOCUMENTS

| 4,501,834 | A | 2/1985 | Su |
| 4,796,646 | A | 1/1989 | Grollier et al. |
| 5,998,500 | A | 12/1999 | Cahill et al. |
| 6,482,394 | B1 | 11/2002 | Schehlmann et al. |
| 7,048,770 | B2 * | 5/2006 | Azizova et al. ................... 8/405 |
| 7,066,966 | B2 | 6/2006 | Cottard et al. |
| 7,147,672 | B2 | 12/2006 | Cottard et al. |
| 2003/0171246 | A1 | 9/2003 | Boeckh et al. |
| 2011/0044924 | A1 | 2/2011 | Verboom et al. |
| 2011/0219552 | A1 | 9/2011 | Zhou et al. |

FOREIGN PATENT DOCUMENTS

| WO | 2005087191 A1 | 9/2005 |
| WO | 2010133573 A2 | 11/2010 |

OTHER PUBLICATIONS

STIC Search Report dated May 28, 2014.*
Arndt Schlosser; 'Silicones Used in Permanent and Semi-Permanent Hair Dyes to Reduce the Fading and Color Change Process of Dyed Hair Occuring by Wash-Out or UV Radiation'; J. Cosmetic Sci. Bd. 55; Feb. 2004, pp. 123-131.
Anonymous: "Polyquaternium-91", Personal Care Products Council , XP002699622, Gefunden im Internet: URL:http:// gov.personalcarecouncil.org/jsp/gov/IngredientDetail.jsp?monoid=23746 [gefunden am Jun. 26, 2013]; pages.
Database GNPD [Online] MINTEL; Conditioner; Feb. 2009, "Conditioner", XP002699621, Database accession No. 1048206; http://www.gnpd.com; pp. 1-3.
Kh. Schrader: 'Grundlagen und Rezepturen der Kosmetika', (translation Basics and recipes of cosmetics), 2., verbesserte und erweiterte Auflage, 1989, Huthig Buch Verlag Heidelberg, pjs 1-20 (book table of contents), English abstract machine translation only.
Becker et al; Safety Assessment of Trimoniums as Used in Cosmetics; International Journal of Toxicology 31 (supplement 3) pp. 296-341; Nov. 2012.

* cited by examiner

*Primary Examiner* — Eisa Elhilo
(74) *Attorney, Agent, or Firm* — Steven L. Nichols; Van Cott, Bagley, Cornwall & McCarthy P.C.

(57) ABSTRACT

An agent for coloring keratinic fibers included in a cosmetic carrier includes at least one cationic acrylic acid ester copolymer including at least one structural unit of the general formula (I), at least one structural unit of the general formula (II), and at least one structural unit of the general formula (III), in which R1, R2, R3, R4, R6 mutually independently denote a hydrogen atom or a C1 to C6 alkyl group, R5, R5', R5" mutually independently denote a C1 to C20 alkyl group, a C2 to C6 alkenyl group, or a C2 to C6 hydroxyalkyl group, R7 denotes a C1 to C6 alkyl group, a C2 to C6 hydroxyalkyl group, or a C2 to C6 polyhydroxyalkyl group, n denotes an integer from 1 to 50,000, m denotes an integer from 2 to 6, $X^-$ denotes a physiologically acceptable anion. The agent further includes at least one color-changing compound.

17 Claims, No Drawings

COLOR INTENSIFICATION BY POLYQUATERNIUM

RELATED DOCUMENTS

The present application claims benefit and is a continuation of International Application No. PCT/EP2012/069979, filed Oct. 9, 2012, which claims the benefit of the filing date of German Patent Application No. 10 2011 085 754.0 filed Nov. 4, 2011. These applications are incorporated herein by reference in their entireties.

DETAILED DESCRIPTION

The present compositions relate to agents for coloring and/or lightening keratinic fibers, in particular human hair, which include special cationic acrylic acid ester copolymers. The compositions further relate to the use of these agents to improve color absorption in the context of the coloring of keratinic fibers, to the use thereof in order to improve the washing stability of colored keratinic fibers, and to a corresponding method.

Human hair may be treated in many ways with hair-cosmetic preparations. These include, for example, cleaning the hair with shampoos, care and regeneration with rinses and therapies, and bleaching, coloring, and shaping the hair using coloring agents, tinting agents, waving agents, and styling preparations. Agents for modifying or toning the color of head hair play a predominant role in hair treatment.

In addition to hair-bleaching agents, which produce oxidative lightening of the hair by breaking down the natural hair dyes, substantially three types of hair coloring agents are used in coloring hair. For permanent, intense color results with corresponding fastness properties, oxidizing coloring agents may be used. Such coloring agents usually include oxidation dye precursors called "developer components" and "coupler components." The developer components, under the influence of oxidizing agents or atmospheric oxygen, form the actual dyes with one another or by coupling to a number of coupler components. Oxidizing coloring agents are notable for outstanding, long-lasting color results. For natural-looking colors, however, a mixture of a larger number of oxidation dye precursors may be used. In many cases, substantive dyes are also used for toning.

For temporary coloring, coloring or tinting agents that include "substantive" agents may be used as a coloring component. These substantive agents are dye molecules that absorb directly onto the hair and do not require an oxidative process in order to form the color. These dyes include, for example, henna, which has been known since antiquity for coloring the body and hair. These colors are, as a rule, appreciably more sensitive to shampooing than the oxidative colors, so that an often-undesired shift in tone, or even visible "decoloring," occurs relatively more quickly than oxidative colors.

Lastly, a novel coloring method has attracted much attention recently. In this method, precursors of the natural hair dye called melanin are applied onto the hair. These precursors form bioanalogous dyes in the context of oxidative processes. For example, 5,6-dihydroxyindoline is used as a dye precursor in such methods. When agents having 5,6-dihydroxyindoline are used, in particular repeatedly, it is possible to restore the natural hair color to people with graying hair. Coloring may occur using atmospheric oxygen as the only oxidizing agent, so that no further oxidizing agents need to be utilized. For persons originally having medium-blonde to brown hair, indoline may be used as the only dye precursor. For use on persons having originally a red and, in particular, a dark to black hair color, on the other hand, satisfactory results may often be achieved only with the concurrent use of further dye components, in particular special oxidation dye precursors.

After the coloring process, hair is exposed to a wide variety of environmental stresses over a long period of time. These extend from everyday weathering of the hair, for example by sunlight and hair washing, to mechanical stresses brought about by styling, to chemical influences if the consumer subjects the hair to a subsequent hair coloring or shaping process. Environmental influences have considerable effects not only on the hair structure itself but also on the dyes present in the hair after the coloring process. The dyes may be bleached out by light exposure, or may be washed out of the hair by perspiration or shampooing. These properties are referred to as the "fastness" properties of the dyes. If the dyes formed or directly used in the course of color formation have appreciably different fastness properties (e.g. UV stability, perspiration resistance, washing resistance, etc.), a detectable and therefore undesired color shift may then occur over time. Both the occurrence of color shifts and, in particular, the fading of the color caused by washing, are not desired by the consumer.

There are various possibilities for reducing the loss of hair color intensity caused by repeated washing. The intensity decrease perceived by the customer may be delayed by striving for a color result that is as intense as possible from the outset. A second possibility is to improve color retention by using active agents that inhibit or reduce the process by which dyes are washed out. It is particularly advantageous to discover an active agent or active-agent combination that both improves the color absorption capability of the dyes during the coloring process and minimizes the degree to which they are later washed out upon subsequent shampooing.

An object of the present invention is therefore to furnish agents for coloring and/or lightening keratinic fibers that improve color absorption during coloring and intensify the penetration of dyes or dye precursors into the keratinic fibers. A further intention is to prevent or minimize washing out of the dyes in the course of repeated shampooing. The agents according to the present invention are intended to improve color intensity and washing fastness without thereby having the disadvantages that are inherent in the coloring agents already known from the existing art.

A further intention is also to achieve, with these agents, color results that exhibit an advantageous application-engineering profile in terms of their further fastness properties, for example their light, friction, perspiration, and cold-waving fastness. Lastly, it is particularly desirable to furnish coloring agents having a good equalization capability.

Optimizing color retention is very important in the cosmetics market, and a variety of color-protecting shampoos or conditioners already exist on the market. The existing art discloses a variety of substances that are used to protect the color of previously colored hair. Polymers, in particular, are used with this purpose.

"Silicones Used in Permanent and Semi-Permanent Hair Dyes to Reduce the Fading and Color Change Process of Dyed Hair Occurring by Wash-Out or UV Radiation," J. Cosmetic Sci. (2004) 55 (Supplement), pp. 123-131, describes the use of silicones to improve color retention. U.S. Pat. No. 7,066,966 and U.S. Pat. No. 7,147,672 disclose an oxidative composition having good washing fastness values, including a cationic polyvinyl lactam. US 2011/0219552 A1 discloses a method for protecting colored hair from washing out by using hydrophobized cationic polymers. Lastly, US 2011/0044924 relates to agents and methods for increasing the color intensity of, and protecting the color of, colored hair, which include quaternary ammonium salts.

The use of these polymers known from the existing art often entails disadvantages, however. It has now been found, surprisingly, that hair treatment agents including special cationic acrylic acid ester copolymers achieve the objects described above without being afflicted with the disadvantages known from the existing art.

A first subject of the present invention is therefore agents for coloring and/or lightening keratinic fibers, in particular human hair, including in a cosmetic carrier at least one cationic acrylic acid ester copolymer including at least one structural unit of the general formula (I), at least one structural unit of the general formula (II), and at least one structural unit of the general formula (III) as depicted below:

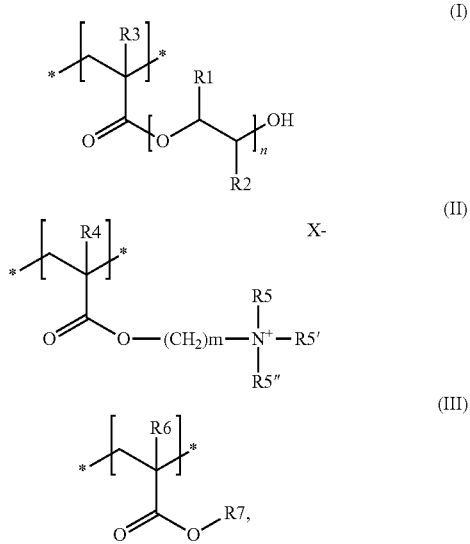

in which
R1, R2, R3, R4, R6 mutually independently denote a hydrogen atom or a $C_1$ to $C_6$ alkyl group,
R5, R5', R5" mutually independently denote a $C_1$ to $C_{20}$ alkyl group, a $C_2$ to $C_6$ alkenyl group, or a $C_2$ to $C_6$ hydroxyalkyl group,
R7 denotes a $C_1$ to $C_6$ alkyl group, a $C_2$ to $C_6$ hydroxyalkyl group, or a $C_2$ to $C_6$ polyhydroxyalkyl group,
n denotes an integer from 1 to 50,000,
m denotes an integer from 2 to 6, and
$X^-$ denotes a physiologically acceptable anion.
The agent further comprises at least one color-changing compound.

"Keratin-including fibers" are understood in principle as all animal hair, e.g. wool, horsehair, angora wool, furs, feathers, and products or textiles produced therefrom. Preferably, however, the keratinic fibers are human hairs.

The term "coloring of keratin fibers" used according to the present invention comprises any form of modification of the color of the fibers. The color changes embraced under the terms "tinting," "lightening," "hair-bleaching,", "bleach," "oxidative coloring," "semipermanent coloring," "permanent coloring," and "temporary coloring" are, in particular, included. Also explicitly included according to the present invention are color changes that exhibit a lighter color result as compared with the initial color, for example coloring hair-bleaching operations.

The agents according to the present invention include as a first essential ingredient at least one cationic acrylic acid ester copolymer including at least one structural unit of the general formula (I), at least one structural unit of the general formula (II), and at least one structural unit of the general formula (III).

Examples of the substituents R1, R2, R3, R4, R5, R5', R5", R6 and R7 recited in formulas (I), (II), and (III) are recited below:

Examples of $C_1$ to $C_6$ alkyl groups are —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$(CH_2)_4CH_3$, —$(CH_2)_5CH_3$. Particularly alkyl residues may include methyl and ethyl. Examples of $C_6$ to $C_{20}$ alkyl groups are hexyl, heptyl, octyl, nonyl, decyl, dodecyl, tetradecyl, pentadecyl, hexadecyl, heptadecyl, octadecyl, nonadecyl, and eicosyl. Examples of $C_2$ to $C_6$ alkenyl groups are vinyl, prop-2-enyl (allyl), 2-methylprop-2-enyl, but-3-enyl, but-2-enyl, pent-4-enyl, or pent-3-enyl. Examples of $C_2$ to $C_6$ hydroxyalkyl groups are —$CH_2CH_2OH$, —$CH_2CH_2CH_2OH$, —$CH_2CH(OH)CH_3$, —$CH_2CH_2CH_2CH_2OH$. In another example, the hydroxyalkyl group is the —$CH_2CH_2OH$ group. Examples of $C_2$ to $C_6$ polyhydroxyalkyl groups are 1,2-dihydroxyethyl, 2,3-dihydroxypropyl, 3,4-dihydroxybutyl and 2,4-dihydroxybutyl.

In one example, the residues R1, R3, and R3 of the structural unit of the general formula (I) mutually independently denote a methyl group or a hydrogen atom; particularly preferably, R1, R2, and R3 denote a hydrogen atom.

It is further preferred if the residues R4 and R6 of the structural units of the general formulas (II) and (III) mutually independently denote a $C_1$ to $C_6$ alkyl group. Particularly preferably, both R4 and R6 denote a methyl group.

The residues R5, R5', and R5" of the structural unit of the general formula (II) preferably mutually independently denote a $C_1$ to $C_{20}$ alkyl group. Particularly preferably, at least one of the residues selected from R5, R5', and R5" denotes a methyl group. It is particularly preferred if all three residues R5, R5', and R5" denote a methyl group.

The residue R7 of the structural unit of the general formula (III) preferably denotes a $C_2$ to $C_6$ hydroxyalkyl group. Particularly preferably, the residue R7 denotes a 2-hydroxyethyl group, a 2-hydroxypropyl group, a 3-hydroxypropyl group, a 2-hydroxy-1-methylethyl group, a 3-hydroxy-2-methylpropyl group, a 3-hydroxy-1-methylpropyl group, a 2-hydroxy-1-methylpropyl group, a 2-hydroxybutyl group, a 3-hydroxybutyl group, or a 4-hydroxybutyl group. Particularly preferably, the residue R7 of the structural unit of the general formula (III) denotes a 2-hydroxypropyl group or a 2-hydroxy-1-methylethyl group.

By definition, m denotes an integer from 2 to 6. It is preferred if m denotes 2 or 3. Particularly preferably, m denotes 2.

A particularly preferred embodiment of the first subject of the invention is an agent according to the present invention which is characterized in that the residues R1, R2, and R3 denote a hydrogen atom, residues R4, R5, R5', R5", and R6 denote a methyl group, the residue R7 denotes a $C_2$ to $C_6$ hydroxyalkyl group, and m is equal to 2 or 3.

Preferred and particularly preferred representatives of the cationic acrylic acid ester copolymer included in the agent according to the present invention are characterized in that they include at least one structural unit of the general formula (I), at least one structural unit of the general formula (II), and at least one structural unit of the general formula (III), wherein m is equal to 2 or 3 and the residues R1, R2, R3, R4, R5, R5', R5", R6, R7 denote one of the substituent combinations disclosed with the compounds numbered 1 through 333 in the table (beginning on page 6) of the priority document.

Halide ions, sulfate ions, hydrogen sulfate ions, phosphate ions, methosulfate ions, as well as organic ions such as lactate, citrate, tartrate, and acetate ions are appropriate, for example, as physiologically acceptable counter ions $X^-$. Halide ions, in particular chloride, are preferred.

The agents according to the present invention for coloring and/or lightening keratinic fibers include the cationic acrylic acid ester copolymer or copolymers, based on their weight, in a total quantity from 0.001 to 25%, preferably 0.01 to 15%, particularly preferably 0.1 to 10%, and especially preferably 0.5 to 5%.

A particularly preferred cationic acrylic acid ester copolymer is the one identified by the International Nomenclature of Cosmetic Ingredients (INCI) name Polyquaternium-91.

A further particularly preferred embodiment of the first subject of the invention is therefore an agent for coloring and/or lightening keratinic fibers which is characterized in that it includes as a cationic acrylic acid ester copolymer, based on its weight, 0.001 to 25%, preferably 0.01 to 15%, particularly preferably 0.1 to 10%, and especially preferably 0.5 to 5% Polyquaternium-91.

The agents according to the present invention include at least one color-changing compound as a second essential ingredient. A "color-changing compound" is understood in the context of the present invention as a compound or substance by means of which the color of the keratinic fibers may be changed. This definition embraces both compounds that change the keratinic fibers toward a darker shade and compounds after whose use the keratinic fibers have a color lighter than the original one. The definition of a "color-changing compound" embraces oxidation dye precursors, substantive dyes, dye precursors of bioanalogous dyes, and oxidizing agents.

If the agent according to the present invention includes, besides the cationic acrylic acid ester copolymer, at least one oxidation dye precursor and/or at least one substantive dye as a color-changing compound, this is preferred.

In a further preferred embodiment of the first subject of the invention, the agent for coloring and/or lightening keratinic fibers therefore includes at least one oxidation dye precursor and/or at least one substantive dye as a color-changing compound.

Categorized among the oxidation dye precursors are oxidation dye precursors of the developer type and of the coupler type. Particularly suitable oxidation dye precursors of the developer type are selected from at least one compound from the group constituted from p-phenylenediamine, p-toluoylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, and physiologically acceptable salts thereof.

Particularly suitable oxidation dye precursors of the coupler type are selected from the group constituted from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of said compounds or physiologically acceptable salts thereof.

It has been found in the context of the work leading to this invention that the object of the present invention may be achieved to a particular degree using agents including specific developer/coupler combinations. Agents that include, besides the cationic acrylic acid ester copolymer according to the present invention, specific combinations of oxidation dye precursor products, are therefore particularly preferred.

It is preferred if the agents according to the present invention include, besides the cationic acrylic acid ester copolymer, one of the following developer/coupler combinations: p-toluoylenediamine/resorcinol; p-toluoylenediamine/2-methylresorcinol; p-toluoylenediamine/2-amino-3-hydroxypyridine; p-toluoylenediamine/2,7-dihydroxynaphthalene; p-toluoylenediamine/3-aminophenol; p-toluoylenediamine/1-naphthol; p-toluoylenediamine/1,5-dihydroxynaphthalene; p-toluoylenediamine/5-amino-2-methylphenol; p-toluoylenediamine/2-(2,4-diaminophenoxy)ethanol; p-toluoylenediamine/3-amino-2-chloro-6-methylphenol; p-toluoylenediamine/2,6-dihydroxy-3,4-dimethylpyridine; p-toluoylenediamine/3-amino-2-methylamino-6-methoxypyridine; p-toluoylenediamine/1,3-bis(2,4-diaminophenyl)propane; 2,4,5,6-tetraminopyrimidine/resorcinol; 2,4,5,6-tetraminopyrimidine/2-methylresorcinol; 2,4,5,6-tetraminopyrimidine/2-amino-3-hydroxypyridine; 2,4,5,6-tetraminopyrimidine/2,7-dihydroxynaphthalene; 4,5-diamino-1-(2-hydroxyethyl)pyrazole/resorcinol; 4,5-diamino-1-(2-hydroxyethyl)pyrazole/2-methylresorcinol; 4,5-diamino-1-(2-hydroxyethyl)pyrazole/2-amino-3-hydroxypyridine; 4,5-diamino-1-(2-hydroxyethyl)pyrazole/2,7-dihydroxynaphthalene; p-aminophenol/resorcinol; p-aminophenol/2-methylresorcinol; p-aminophenol/2-amino-3-hydroxypyridine; p-aminophenol/2,7-dihydroxynaphthalene; p-aminophenol/3-aminophenol; p-aminophenol/1-naphthol; p-aminophenol/1,5-dihydroxynaphthalene; p-aminophenol/5-amino-2-methylphenol; p-aminophenol/2-(2,4-diaminophenoxy)ethanol; p-aminophenol/3-amino-2-chloro-6-methylphenol; p-aminophenol/2,6-dihydroxy-3,4-dimethylpyridine; p-aminophenol/3- amino-2-methylamino-6-methoxypyridine; p-aminophenol/ 1,3-bis(2,4-diaminophenyl)propane.

Particularly preferred agents according to the present invention include, besides the cationic acrylic acid ester copolymer, one of the following combinations of two developers and one coupler: p-toluoylenediamine/2,4,5,6-tetraminopyrimidine/resorcinol; p-toluoylenediamine/2,4,5,6-tetraminopyrimidine/2-methylresorcinol; p-toluoylenediamine/ 2,4,5,6-tetraminopyrimidine/2-amino-3-hydroxypyridine; p-toluoylenediamine/2,4,5,6-tetraminopyrimidine/2,7-dihydroxynapthalene.

Particularly good color intensification or particularly good color retention is achieved in particular when the keratinic fibers are colored with a formulation including the combination p-toluoylenediamine, 2,4,5,6-tetraminopyrimidine, resorcinol, 2-methylresorcinol, 2-amino-3-hydroxypyridine, and 2,7-dihydroxynaphthalene.

Developer components and coupler components are generally used in approximately molar quantities with respect to one another. Although molar utilization has proven useful, a certain excess of individual oxidation dye precursors is not disadvantageous, so that developer components and coupler components may exhibit a molar ratio from 1 to 0.5 to 1 to 3, in particular 1 to 1 to 1 to 2.

In the context of a further preferred embodiment, the agent according to the present invention includes at least one substantive dye as a color-changing compound. Substantive dyes are dyes that absorb directly onto the hair and do not require an oxidative process for the formation of color. Substantive dyes are usually nitrophenylenediamines, nitroaminophenols, azo dyes, anthraquinones, or indophenols.

Substantive dyes may be subdivided into anionic, cationic, and nonionic substantive dyes, which are selected and employed by one skilled in the art in accordance with the requirements of the carrier base.

Preferred anionic substantive dyes are the compounds referred to by international designations or trade names as bromophenol blue, tetrabromophenol blue, Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, and Acid Black 52.

Preferred cationic substantive dyes are Basic Blue 7, Basic Blue 26, Basic Violet 2, and Basic Violet 14, Basic Yellow 57, Basic Red 76, Basic Blue 16, Basic Blue 347 (Cationic Blue 347/Dystar), Basic Blue 99, Basic Brown 16, and Basic Brown 17, as well as Basic Yellow 87, Basic Orange 31, and Basic Red 51.

Nonionic nitro and quinone dyes, and neutral azo dyes, are particularly suitable as nonionic substantive dyes. Preferred nonionic substantive dyes are the compounds referred to by international designations or commercial names as HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-3-nitrophenyl)amino]benzoic acid, 4-[(3-hydroxypropylamino]-3-nitrophenol, 4-nitro-o-phenylenediamine, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

It is preferred if the agent according to the present invention includes as a color-changing compound the substantive dye 4-amino-3-nitrophenol, alone or in combination with further color-changing compounds.

In a further preferred embodiment the agents according to the present invention include, as color-changing compounds, both a substantive dye and an oxidation dye precursor of the developer type and/or coupler type.

The agent according to the present invention may furthermore include at least one dye precursor of a bioanalogous dye as a color-changing compound. It is preferred to use, as dye precursors of bioanalogous dyes, indoles and indolines that comprise at least two groups selected from hydroxy and/or amino groups, preferably as a substituent on the six-membered ring. These groups may carry further substituents, for example in the form of an etherification or esterification of the hydroxy group, or an alkylation of the amino group.

Compositions according to the present invention that include precursors of bioanalogous dyes are preferably used as air-oxidizing coloring agents. In this embodiment, an additional oxidizing agent is consequently not added to said compositions.

Particularly preferred derivatives of indoline are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, and 5,6-dihydroxyindoline-2-carboxylic acid.

Particularly preferred derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, and 5,6-dihydroxyindole-2-carboxylic acid.

The agent according to the present invention includes at least one color-changing compound in a respective weight proportion from 0.001 to 12%. If the color-changing agent involves oxidation dye precursors, substantive dyes, and/or precursors of bioanalogous dyes, they are preferably employed respectively in a quantity from 0.01 to 10 wt %, particularly preferably from 0.1 to 5 wt %, and especially preferably from 0.25 to 3 wt %, based on the ready-to-use agent.

A further particularly preferred embodiment of the first subject of the invention is therefore an agent for coloring and/or lightening keratinic fibers which is characterized in that it includes as a color-changing compound at least one oxidation dye precursor and/or at least one substantive dye respectively in a quantity from 0.001 to 12 wt %, preferably from 0.01 to 10 wt %, particularly preferably from 0.1 to 5 wt %, and especially preferably from 0.25 to 3 wt %, based on the ready-to-use agent.

The agents according to the present invention may furthermore be employed as lightening coloring agents or as lightening agents. In order to achieve the lightening effect the agents include for this purpose an oxidizing agent as a color-changing agent. Hydrogen peroxide and/or a solid addition product thereof with organic or inorganic compounds is preferably used as an oxidizing agent. Examples of such addition products are addition products with urea, melamine, and sodium borate.

In a preferred embodiment, hydrogen peroxide itself is used as an aqueous solution. The concentration of a hydrogen peroxide solution in the agent according to the present invention is determined on the one hand by legislative provisions and on the other hand by the desired effect. In one example, 6- to 12-wt % solutions in water are preferably used.

Ready-to-use agents of the first subject of the invention that are preferred according to the present invention are characterized in that they include the oxidizing agent in a quantity from 0.001 to 12 wt %, preferably from 0.01 to 10 wt %, preferably 1 to 9 wt %, particularly preferably 2.5 to 8 wt %, and in particular 3 to 6 wt %, based on the ready-to-use agent.

A further particularly preferred embodiment of the first subject of the invention is therefore an agent for coloring and/or lightening keratinic fibers which is characterized in that it includes as a color-changing compound at least one oxidizing agent selected from hydrogen peroxide and solid addition products thereof with organic or inorganic compounds, in a quantity from 0.001 to 12 wt %, preferably from 0.01 to 10 wt %, preferably 1 to 9 wt %, particularly preferably 2.5 to 8 wt %, and in particular 3 to 6 wt %, based on the ready-to-use agent.

Oxidizing agent preparations of this kind are preferably aqueous flowable oxidizing agent preparations. Preferred preparations are characterized in that the flowable oxidizing agent preparation includes, based on its weight, 40 to 90 wt %, preferably 50 to 85 wt %, particularly preferably 55 to 80 wt %, more preferably 60 to 77.5 wt %, and in particular 65 to 75 wt % water.

In a further preferred embodiment the agents according to the present invention therefore include as color-changing compounds both an oxidation dye precursor of the developer type and/or coupler type and an oxidizing agent.

In order to achieve an intensified lightening and bleaching effect, the agent may furthermore include at least one peroxo salt. Suitable peroxo salts are inorganic peroxo compounds preferably selected from the group constituted from ammonium peroxodisulfate, alkali metal peroxodisulfates, ammonium peroxomonosulfate, alkali metal peroxomonosulfates, alkali metal peroxodiphosphates, and alkaline earth metal peroxides. Peroxodisulfates are particularly preferred, in particular ammonium peroxodisulfate, potassium peroxodisulfate, and sodium peroxodisulfate.

A further preferred embodiment of the first subject of the invention is therefore an agent according to the present invention which is characterized in that it additionally includes, based on its weight, 0.01 to 30% of a bleaching power intensifier selected from ammonium peroxodisulfate, potassium peroxodisulfate, sodium peroxodisulfate, potassium hydrogen peroxomonosulfate, potassium peroxodiphosphate, magnesium peroxide, and barium peroxide.

If the agents additionally include persulfates, said persulfates are then included in the agent at a proportion of 0.01 to 30 wt %, preferably 1.5 to 28 wt %, by preference 2.0 to 25 wt %, and in particular 5 to 20 wt %, based in each case on the total weight of the agent.

In order to intensify the hair-bleaching effect, the agent may include further bleaching power intensifiers such as tetraacetylethylendiamine (TAED), 1,5-diacetyl-2,4-dioxohexahydro-1,3,5-triazine (DADHT), tetraacetyl glycoluril (TAGU), N-nonanoyl succinimide (NOSI), n-nonanoyl or isononanoyl oxybenzenesulfonate (n- or iso-NOBS), phthalic acid anhydride, triacetin, ethylene glycol diacetate, and 2,5-diacetoxy-2,5-dihydrofuran, as well as carbonate salts or hydrogen carbonate salts, in particular ammonium hydrogen carbonate, ammonium carbonate, sodium hydrogen carbonate, disodium carbonate, potassium hydrogen carbonate, dipotassium carbonate, and calcium carbonate, and nitrogen-including heterocyclic bleaching power intensifiers such as 4-acetyl-1-methylpyridinium-p-toluenesulfonate, 2-acetyl-1-methylpyridinium-p-toluenesulfonate, and N-methyl-3,4-dihydroisoquinolinium-p-toluenesulfonate.

To further enhance the lightening, the composition according to the present invention may additionally have at least one $SiO_2$ compound, such as silicic acid or silicates, in particular water glasses, added to it. It may be preferred according to the present invention to utilize the $SiO_2$ compounds in quantities from 0.05 wt % to 15 wt %, particularly preferably in quantities from 0.15 wt % to 10 wt %, and very particularly preferably in quantities from 0.2 wt % to 5 wt %, based in each case on the anhydrous composition according to the present invention. The quantity indications reflect in each case the concentration of the $SiO_2$ compounds (without their water component) in the agents.

It has furthermore proven to be advantageous if the oxidizing agent preparations include at least one stabilizer or complexing agent. Common complexing agents and stabilizers that are preferred in the context of the present invention are, for example, polyoxycarboxylic acids, polyamines, ethylenediaminetetraacetic acid (EDTA), N-hydroxyethylethylenediaminetriacetic acid, diethylenetriaminepentaacetic acid (DTPA), ethylenediaminedisuccinic acid (EDDS), hydroxyethyliminodiacetic acid, nitridodiacetic acid-3-propionic acid, isoserinediacetic acid, N,N-di-(2-hydroxyethyl)glycine, N-(1,2-dicarboxy-2-hydroxyethyl)glycine, N-(1,2-dicarboxy-2-hydroxyethyl)aspartic acid or nitrilotriacetic acid (NTA), ethylenediaminediglutaric acid (EDGA), 2-hydroxypropylenediaminedisuccinic acid (HPDS), glycinamide-N,N'-disuccinic acid (GADS), ethylendiamine-N—N'-diglutaric acid (EDDG), 2-hydroxypropylenediamine-N—N'-disuccinic acid (HPDDS), diaminoalkyldi(sulfosuccinic acid) (DDS), ethylenedicysteic acid (EDC), ethylenediamine-N—N'-bis(orthohydroxyphenyl)acetic acid (EDDHA), N-2-hydroxyethylamine-N,N-diacetic acid, glyceryliminodiacetic acid, iminodiacetic acid-N-2-hydroxypropylsulfonic acid, aspartic acid-N-carboxymethyl-N-2,5-hydroxypropyl-3-sulfonic acid, β-alanine-N,N'-diacetic acid, aspartic acid-N,N'-diacetic acid, aspartic acid-N-monoacetic acid, dipicolinic acid, as well as salts and/or derivatives thereof; geminal diphosphonic acids such as 1-hydroxyethane-1,1-diphosphonic acid (HEDP), higher homologs thereof having up to 8 carbon atoms, and hydroxy- or amino-group—including derivatives thereof, and 1-aminoethane-1,1-diphosphonic acid, higher homologs thereof having up to 8 carbon atoms, and hydroxy- or amino-group—including derivatives thereof; aminophosphonic acids such as ethylenediaminetetra(methylenephosphonic acid) (EDTMP), diethylenetriaminepenta(methylenephosphonic acid) (DTPMP) and higher homologs thereof, or nitrilotri(methylenephosphonic acid), phosphonopolycarboxylic acids such as 2-phosphonobutane-1,2,4-tricarboxylic acid; cyclodextrins and alkali stannates (sodium stannate), alkali pyrophosphates (tetrasodium pyrophosphate, disodium pyrophosphate), alkali phosphates (sodium phosphate), and phosphoric acid, as well as salts thereof.

In order to prevent a premature, undesired reaction of the oxidation dye precursors as a result of the oxidizing agents, the oxidation dye precursors and oxidizing agents themselves are usefully packaged separately from one another and brought into contact immediately before use.

In a further embodiment of the present invention, agents which are characterized in that they are produced immediately before use by mixing at least two preparations are therefore preferred, wherein the at least two preparations are furnished in at least two separately packaged containers, and wherein one container includes an agent (A) that includes in a cosmetic carrier at least one cationic acrylic acid ester copolymer according to the present invention, and a further container includes an oxidizing agent preparation (B) including at least one oxidizing agent.

In this case, any substantive dyes and/or oxidation dye precursors of the developer type and/or coupler type that may additionally be included are advantageously packaged in agent (A) together with the cationic acrylic acid ester copolymer according to the present invention.

In a further embodiment of the present invention, agents which are characterized in that they are produced immediately before use by mixing at least two preparations are preferred, wherein the at least two preparations are furnished in at least two separately packaged containers, and wherein one container includes an agent (A) that includes in a cosmetic carrier at least one cationic acrylic acid ester copolymer according to the present invention, and a further container includes an oxidizing agent preparation (B) including at least one color-changing compound.

The agents according to the present invention include the cationic acrylic acid ester copolymers and/or the color-changing compound(s) in a cosmetic carrier, preferably in a suitable aqueous, alcoholic, or aqueous alcoholic carrier. For purposes of hair coloring such carriers are, for example, creams, emulsions, gels, or also surfactant-including foaming solutions such as shampoos, foam aerosols, foam formulations, or other preparations that are suitable for utilization on hair. It is also conceivable, however, to integrate the agents according to the present invention into a powdered or also tablet-shaped formulation.

"Aqueous alcoholic" solutions are understood for purposes of the present invention as aqueous solutions including 3 to 70 wt % of a $C_1$ to $C_4$ alcohol, in particular ethanol or isopropanol. The agents according to the present invention may additionally include further organic solvents, for example methoxybutanol, benzyl alcohol, ethyl diglycol, or 1,2-propylene glycol. All water-soluble organic solvents are preferred in this context.

The coloring preparation and, optionally, the oxidizing agent preparation include further adjuvants and additives. It has proven advantageous according to the present invention, for example, if the coloring preparation and/or oxidizing agent preparation include at least one thickening agent. No restrictions exist in principle regarding these thickening agents. Both organic and entirely inorganic thickening agents may be utilized.

According to a first preferred embodiment the thickening agent is an anionic synthetic polymer. Preferred anionic groups are the carboxylate group and the sulfonate group.

Examples of anionic monomers from which the polymeric anionic thickening agents may be made are acrylic acid, methacrylic acid, crotonic acid, itaconic acid, maleic acid anhydride, and 2-acrylamide-2-methylpropanesulfonic acid. The acid groups may be present entirely or in part as a sodium, potassium, ammonium, or mono- or triethanolammonium salt. Preferred monomers are maleic acid anhydride and, in particular, 2-acrylamido-2-methylpropanesulfonic acid and acrylic acid.

It was found in the context of the work leading to the present invention that advantageous properties were obtained in particular when the agent according to the present invention additionally includes at least one anionic acrylic acid polymer and/or one anionic acrylic acid copolymer.

The anionic acrylic acid polymer and/or anionic acrylic acid copolymer may be included in the agent according to the present invention at a weight proportion from 0.001 to 20%, preferably 0.01 to 10%, and particularly preferably from 0.5 to 5%.

A further preferred embodiment of the first subject of the invention is therefore an agent according to the present invention which is characterized in that it additionally includes, based on its weight, 0.001 to 20% of at least one anionic acrylic acid polymer and/or one anionic acrylic acid copolymer.

It may be preferred in this connection if the anionic acrylic acid copolymer additionally included in the agent according to the present invention is a copolymer that is produced by copolymerization of the monomers acrylic acid (prop-2-enoic acid), methacrylic acid (2-methylprop-2-enoic acid), acrylic acid methyl ester (methyl prop-2-enoate), methacrylic acid methyl ester (methyl 2-methylprop-2-enoate), acrylic acid ethyl ester (ethyl prop-2-enoate), methacrylic acid ethyl ester (ethyl 2-methylprop-2-enoate), acrylic acid-n-butyl ester (butyl prop-2-enoate), methacrylic acid-n-butyl ester (butyl 2-methylprop-2-enoate), ethene, and/or styrene (ethenylbenzene).

According to a preferred embodiment, the agent according to the present invention additionally includes an anionic acrylic acid copolymer that is produced by copolymerization of the monomers methacrylic acid (2-methylprop-2-enoic acid), methacrylic acid methyl ester (methyl 2-methylprop-2-enoate), acrylic acid ethyl ester (ethyl prop-2-enoate), acrylic acid-n-butyl ester (butyl prop-2-enoate), ethene, and/or styrene (ethenylbenzene).

According to a very particularly preferred embodiment, the agent according to the present invention additionally includes an anionic acrylic acid copolymer that is produced by copolymerization of the monomers methacrylic acid (2-methylprop-2-enoic acid), methacrylic acid methyl ester (methyl 2-methylprop-2-enoate), acrylic acid ethyl ester (ethyl prop-2-enoate), acrylic acid-n-butyl ester (butyl prop-2-enoate), ethene, and styrene (ethenylbenzene).

A particularly preferred anionic acrylic acid copolymer is the one referred to by the INCI name Polyacrylate-15.

A further particularly preferred embodiment of the first subject of the invention is therefore an agent according to the present invention that is characterized in that it includes Polyacrylate-15 as an anionic acrylic acid copolymer.

In a further embodiment the agent according to the present invention may include anionic homopolymers as anionic polymers. Preferred anionic homopolymers are uncrosslinked and crosslinked polyacrylic acids. Allyl ethers of pentaerythritol, of sucrose, and of propylene may be preferred crosslinking agents. Such compounds are obtainable commercially, for example, under the tradename CARBOPOL. CARBOPOL is a polymer developed and distributed by Lubrizol Corporation. Also preferred is the homopolymer of 2-acrylamido-2-methylpropanesulfonic acid that is obtainable commercially, for example, under the designation RHEOTHIK 11-80 developed and distributed by BASF Societas Europaea.

Within a further embodiment it may likewise be preferred to employ copolymers of at least one anionic monomer and at least one nonionogenic monomer. With regard to the anionic monomers, reference is made to the substances discussed above. Preferred nonionogenic monomers are acrylamide, methacrylamide, acrylic acid esters, methacrylic acid esters, itaconic acid mono- and diesters, vinylpyrrolidinone, vinyl ethers, and vinyl esters.

Further preferred anionic copolymers are, for example, copolymers of acrylic acid, methacrylic acid, or $C_1$ to $C_6$ alkyl esters thereof, such as those marketed under the INCI declaration Acrylates Copolymers. A preferred commercial product is, for example, ACULYN 33 copolymer developed and distributed by Rohm & Haas Company. Also preferred, however, are copolymers of acrylic acid, methacrylic acid, or $C_1$ to $C_6$ alkyl esters thereof and the esters of an ethylenically unsaturated acid and an alkoxylated fatty alcohol. Suitable ethylenically unsaturated acids are in particular acrylic acid, methacrylic acid, and itaconic acid; suitable alkoxylated fatty alcohols are in particular steareth-20 or ceteth-20. Copolymers of this kind are marketed under the commercial name ACULYN 22 copolymer developed and distributed by Rohm & Haas Company, and STRUCTURE 2001 copolymer and STRUCTURE 3001 copolymer developed and distributed by the Ingredion Incorporated.

Preferred anionic copolymers are furthermore acrylic acid/acrylamide copolymers and, in particular, polyacrylamide copolymers having sulfonic acid group-including monomers. A particularly preferred anionic copolymer is made up of 70 to 55 mol % acrylamide and 30 to 45 mol % 2-acrylamide-2-methylpropanesulfonic acid, the sulfonic acid group being present entirely or in part as a sodium, potassium, ammonium, or mono- or triethanolammonium salt. This copolymer may also be present in crosslinked fashion with polyolefinically unsaturated compounds such as tetraallyloxyethane, allylsucrose, allylpentaerythritol, and methylene bisacrylamide preferably being employed as crosslinking agents. One such polymer is included in the commercial products SEPIGEL 305 polymer and SIMUGEL 600 polymer developed and distributed by SEPPIC Company. The use of these compounds, which, besides the polymer component, include a hydrocarbon mixture ($C_{13}$ to $C_{14}$ isoparaffin or isohexadecane) and a nonionic emulsifier agent (Laureth-7 or Polysorbate-80), has proven particularly advantageous in the context of the teaching of the present invention.

Polymers of maleic acid anhydride and methyl vinyl ether, in particular those having crosslinks, are also preferred thickening agents. A maleic acid/methyl vinyl ether copolymer crosslinked with 1,9-decadiene is obtainable commercially under the name STABILEZE QM copolymer developed and distributed by Ashland Incorporated.

The agent according to the present invention may preferably additionally include at least one further anionic polymerizate or copolymerizate of acrylic acid and/or methacrylic acid. Preferred polymerizates of this kind are:

polymerizates of, for example, at least 10 wt % acrylic acid-low alkyl esters, 25 to 70 wt % methacrylic acid, and, optionally, up to 40 wt % of a further comonomer, mixed polymerizates made up of 50 to 75 wt % ethyl acrylate, 25 to 35 wt % acrylic acid, and 0 to 25 wt % further comonomers. Suitable dispersions of this kind are commercially obtainable, for example under the commercial name LATEKOLL D developed and distributed by BASF Societas Europaea.

copolymerizates made up of 50 to 60 wt % ethyl acrylate, 30 to 40 wt % methacrylic acid, and 5 to 15 wt % acrylic acid, crosslinked with ethylene glycol dimethacrylate.

According to a further embodiment the thickening agent is a cationic synthetic polymer that differs from the cationic polymers according to the present invention. Preferred cationic polymers are:

homopolymers of the general formula (HP-1),

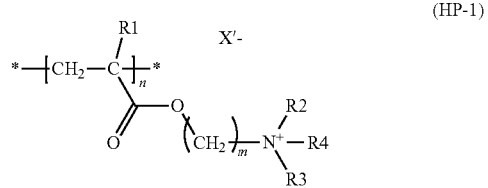

(HP-1)

in which R1=—H or —$CH_3$, R2, R3, and R4 are selected mutually independently from $C_1$ to $C_4$ alkyl, alkenyl, or hydroxyalkyl groups, m=1, 2, 3, or 4, n is a natural number, and $X^-$ is a physiologically acceptable organic or inorganic anion, are particularly preferred cationic polymeric gel formers. In the context of these polymers, those for which at least one of the following conditions applies:

R1 denotes a methyl group,
R2, R3, and R4 denote methyl groups, and
m has the value of 2 are particularly preferred according to the present invention.

Appropriate physiologically acceptable counterions $X'^-$ are, for example, halide ions, sulfate ions, phosphate ions, methosulfate ions, and organic ions such as lactate, citrate, tartrate, and acetate ions. Halide ions, in particular chloride, are preferred.

A particularly suitable homopolymer is the poly(methacryloxyethyltrimethylammonium) chloride (crosslinked, if desired) having the INCI name Polyquaternium-37. The crosslinking may be accomplished, if desired, with the aid of olefinically polyunsaturated compounds, for example divinylbenzene, tetraallyloxyethane, methylene bisacrylamide, diallyl ether, polyallylpolyglyceryl ether, or allyl ethers of sugars or sugar derivatives such as erythritol, pentaerythritol, arabitol, mannitol, sorbitol, sucrose, or glucose. Methylene bisacrylamide is a preferred crosslinking agent.

The homopolymer is preferably used in the form of a nonaqueous polymer dispersion that should comprise a polymer proportion not less than 30 wt %. Such polymer dispersions are obtainable commercially under the designations SALCARE SC 95 polymer dispersion (approx. 50% polymer proportion, further components: mineral oil (INCI name: Mineral Oil) and tridecylpolyoxypropylenepolyoxyethylene ether (INCI name: P PG-1-Trideceth-6)), and SALCARE SC 96 polymer dispersion (approx. 50% polymer proportion, further components: mixture of diesters of propylene glycol with a mixture of caprylic and capric acid (INCI name: Propylene Glycol Dicaprylate/Dicaprate) and tridecylpolyoxypropylenepolyoxyethylene ether (INCI name: PPG-1-Trideceth-6)), both developed and distributed by BASF Societas Europaea.

In a further preferred embodiment, naturally occurring thickening agents are used. Preferred thickening agents of this embodiment are, for example, nonionic guar gums. Both modified and unmodified guar gums may be employed according to the present invention. Unmodified guar gums are marketed, for example, under the commercial name JAGUAR C, and are developed and distributed by the Rhone-Poulenc Company. Modified guar gums preferred according to the present invention include $C_1$ to $C_6$ hydroxyalkyl groups. The hydroxymethyl, hydroxyethyl, hydroxypropyl, and hydroxybutyl groups are preferred. Guar gums modified in this fashion are known in the existing art and may be produced, for example, by reacting the guar gums with alkylene oxides. The degree of hydroxyalkylation, which corresponds to the number of alkylene oxide molecules consumed in terms of the number of free hydroxy groups on the guar gums, is preferably between 0.4 and 1.2. Guar gums modified in this fashion are obtainable commercially under the commercial names JAGUAR HP8, JAGUAR HP60, JAGUAR HP120, JAGUAR DC 293, and JAGUAR HP105 developed and distributed by the Rhone-Poulenc Company.

Further suitable natural thickening agents are also already known from the existing art.

Also preferred according to this embodiment are biosaccharide gums of microbial origin, such as scleroglucan gums or xanthan gums, gums from plant exudates such as gum arabic, ghatti gum, karaya gum, tragacanth gum, carrageenan gum, agar-agar, locust bean flour, pectins, alginates, starch fractions and derivatives such as amylose, amylopectin, and dextrins, cellulose derivatives, e.g. methyl cellulose, carboxyalkyl celluloses, and hydroxyalkyl celluloses.

Preferred hydroxyalkyl celluloses are in particular the hydroxyethyl celluloses marketed under the names CELLOSIZE polymers developed and distributed by the Amerchol Company, and NATROSOL polymer developed and distributed by Ashland Inc. Suitable carboxyalkyl celluloses are in particular the carboxymethyl celluloses marketed under the names BLANOS, AQUASORB, and AMBERGUM developed and distributed by Ashland Inc., and CELLGON developed and distributed by the Montello Company.

Starch and derivatives thereof are also preferred. A corn starch etherified with a 2-hydroxypropyl group, as marketed e.g. by Ingredion Incorporated under the commercial name AMAZE, is particularly advantageous.

Nonionic, fully synthetic polymers, however, for example polyvinyl alcohol or polyvinylpyrrolidone, are also usable as thickening agents according to the present invention. Preferred nonionic, fully synthetic polymers are marketed, for example, by the BASF Societas Europaea under the commercial name LUVISKOL. Besides their outstanding thickening properties, nonionic polymers of this kind also make possible an appreciable improvement in the sensory feel of the resulting preparations.

Sheet silicates (polymeric crystalline sodium disilicates) have proven to be particularly suitable as inorganic thickening agents for purposes of the present invention.

Clays, in particular magnesium aluminum silicates, such as bentonite, in particular smectites such as montmorillonite and hectorite, which optionally may also be suitably modified, and synthetic sheet silicates such as the magnesium sheet silicate marketed by the aid Chemie Company under the commercial designation OPTIGEL, are particularly preferred.

With regard to the optionally hydrated $SiO_2$ compounds, those preferred are silicic acids, oligomers and polymers thereof, and salts thereof. Preferred salts are the alkali salts, in particular the potassium and sodium salts. The sodium salts are very particularly preferred.

The optionally hydrated $SiO_2$ compounds may be present in a variety of forms. The $SiO_2$ compounds are used according to the present invention preferably in the form of silica gels, or particularly preferably as water glass. These $SiO_2$ compounds may be present in part in aqueous solution. Water glasses are also very particularly preferred according to the present invention. Water glasses particularly preferred according to the present invention are marketed, inter alia, by the Henkel AG & Company, KGaA under the designations FERROSIL 119, Sodium Water Glass 40/42, PORTIL A, PORTIL AW and PORTIL W, and by the Akzo Company under the designation BRITESIL C20.

The agent according to the present invention preferably furthermore has an emulsifier agent or surfactant added to the agent. Surface-active substances are referred to as "surfactants" or as "emulsifier agents" depending on their field of application and are selected from anionic, cationic, zwitterionic, amphoteric, and nonionic surfactants and emulsifier agents. These substances are described in detail below.

Preferred anionic surfactants are alkyl sulfates, alkyl ether sulfates, and ethercarboxylic acids having 10 to 18 carbon atoms in the alkyl group and up to 12 glycol ether groups in the molecule.

"Zwitterionic surfactants" refers to those surface-active compounds which carry in the molecule at least one quaternary ammonium group and at least one carboxylate, sulfonate, or sulfate group. Examples of such zwitterionic surfactants are the so-called betaines, such as the N-alkyl-N,N-dimethylammonium glycinates, for example cocalkyldimethylammonium glycinate, N-acylaminopropyl-N,N-dimethylammonium glycinates, for example cocacylaminopropyldimethylammonium glycinate, and 2-alkyl-3-carboxymethyl-3-hydroxyethylimidazolines, having in each case 8 to 18 carbon atoms in the alkyl or acyl group, as well as cocacylaminoethylhydroxyethylcarboxymethyl glycinate. A preferred zwitterionic surfactant is the fatty acid amide derivative referred to by the INCI name Cocamidopropyl Betaine.

"Amphoteric surfactants" are understood to be those surface-active compounds that include in the molecule, in addition to a $C_8$ to $C_{24}$ alkyl or acyl group, at least one free amino group and at least one —COON or —$SO_3H$ group, and are capable of forming internal salts. Examples of suitable amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids, having in each case approximately 8 to 24 carbon atoms in the alkyl group. Particularly preferred amphoteric surfactants are N-cocalkylaminopropionate, cocacylaminoethylaminopropionate, and $C_{12}$ to $C_{18}$ acyl sarcosine.

It has furthermore proven advantageous if the coloring and/or lightening agents according to the present invention include further, nonionogenic surface-active substances. Nonionic surfactants include as a hydrophilic group, for example, a polyol group, a polyalkylene glycol ether group, or a combination of a polyol and polyglycol ether group. Such compounds are, for example"

- addition products of 1 to 50 mol ethylene oxide and/or 0 to 5 mol propylene oxide with linear and branched fatty alcohols having 8 to 30 carbon atoms, for example lauryl alcohol, myristyl alcohol, cetyl alcohol, but also stearyl alcohol, isostearyl alcohol, and oleyl alcohol, with fatty acids having 8 to 30 carbon atoms and with alkylphenols having 8 to 15 carbon atoms in the alkyl group;
- addition products, end-capped with a methyl or $C_2$ to $C_6$ alkyl group, of 1 to 50 mol ethylene oxide and/or 0 to 5 mol propylene oxide with linear and branched fatty alcohols having 8 to 30 carbon atoms, with fatty acids having 8 to 30 carbon atoms, and with alkylphenols having 8 to 15 carbon atoms in the alkyl group, for example the grades obtainable under the marketing designations DEHYDOL LS and DEHYDOL LT developed and distributed by Cognis GmbH;
- polyglycerol esters and alkoxylated polyglycerol esters, for example poly(3)glycerol diisostearate obtainable under the marketing designation LAMEFORM TGI, and poly(2)glycerol polyhydroxystearate obtainable under the marketing designation DEHYMULS PGPH, both developed and distributed by Henkel AG & Company, KGaA;
- polyol fatty acid esters such as, for example, HYDAGEN HSP, or SOVERMOL esters, both developed and distributed by CognisGmbH;
- higher-alkoxylated, preferably propoxylated and in particular ethoxylated mono-, di- and triglycerides, for example glycerol monolaurate+20 ethylene oxide and glycerol monostearate+20 ethylene oxide;
- amine oxides;
- hydroxy mixed ethers;
- sorbitan fatty acid esters and addition products of ethylene oxide with sorbitan fatty acid esters, for example polysorbates and sorbitan monolaurate+20 mol ethylene oxide (EO);

sugar fatty acid esters and addition products of ethylene oxide with sugar fatty acid esters;
addition products of ethylene oxide with fatty acid alkanolamides and fatty amines;
fatty acid N-alkylglucamides;
alkylphenols and alkylphenol alkoxylates having 6 to 21, in particular 6 to 15 carbon atoms in the alkyl chain and 1 to 30 ethylene oxide and/or propylene oxide units. Preferred representatives of this class are, for example, nonylphenol+9 EO and octylphenol+8 EO; and
alkylpolyglycosides corresponding to the general formula $RO-(Z)_x$, wherein R denotes alkyl, Z denotes sugar, and x denotes the number of sugar units. The alkylpolyglycosides usable according to the present invention may include only one specific alkyl residue R. Usually, however, these compounds are produced on the basis of natural fats and oils or mineral oils. In this case, mixtures corresponding to the starting compounds, or corresponding to the respective processing of those compounds, are present as alkyl residues R.

$C_8$ to $C_{22}$ alkylmono- and -oligoglycosides and ethoxylated analogs thereof are particularly suitable as nonionic surfactants. The non-ethoxylated compounds in particular have proven to be particularly suitable.

Those alkylpolyglycosides of formula $RO-(Z)_x$ in which R is made up:
substantially of $C_8$ and $C_{10}$ alkyl groups;
substantially of $C_{12}$ and $C_{14}$ alkyl groups;
substantially of $C_8$ to $C_{16}$ alkyl groups;
substantially of $C_{12}$ to $C_{16}$ alkyl groups; or
substantially of $C_{16}$ to $C_{18}$ alkyl groups are particularly preferred.

These compounds are characterized in that any mono- or oligosaccharides may be used as sugar module Z. Sugars having 5 or 6 carbon atoms, as well as the corresponding oligosaccharides, are usually used. Such sugars are, for example, glucose, fructose, galactose, arabinose, ribose, xylose, lyxose, allose, altrose, mannose, gulose, idose, talose, and sucrose. Preferred sugar modules are glucose, fructose, galactose, arabinose, and sucrose; glucose is particularly preferred.

The alkylpolyglycosides usable according to the present invention include on average 1.1 to 5 sugar units. Alkylpolyglycosides having values of x from 1.1 to 2.0 are preferred. Alkylglycosides in which x is 1.1 to 1.8 are very particularly preferred.

The alkoxylated homologs of the previously mentioned alkylpolyglycosides may also be used according to the present invention. These homologs may include on average up to 10 ethylene oxide and/or propylene oxide units per alkylglycoside unit.

The alkylene oxide addition products with saturated linear fatty alcohols and fatty acids, having respectively 2 to 30 mol ethylene oxide per mol of fatty alcohol or fatty acid, have proven to be further preferred nonionic surfactants. Preparations having outstanding properties are likewise obtained when they include fatty acids of ethoxylated glycerol as nonionic surfactants.

The anionic, nonionic, zwitterionic, or amphoteric surfactants are employed in quantities from 0.1 to 45 wt %, preferably 1 to 30 wt %, and very particularly from 1 to 15 wt %, based on the total quantity of ready-to-use agent.

Also preferred according to the present invention are cationic surfactants of the quaternary ammonium compound, esterquat, and amidoamine types. Preferred quaternary ammonium compounds are ammonium halides, in particular chlorides and bromides, such as alkyltrimethylammonium chlorides, dialkyldimethylammonium chlorides, and trialkylmethylammonium chlorides, for example cetyltrimethylammonium chloride, stearyltrimethylammonium chloride, distearyldimethylammonium chloride, lauryldimethylammonium chloride, lauryldimethylbenzylammonium chloride, and tricetylmethylammonium chloride, as well as the imidazolium compounds referred to by the INCI names Quaternium-27 and Quaternium-83. The long alkyl chains of the aforementioned surfactants preferably have 10 to 18 carbon atoms. Further cationic surfactants usable according to the present invention are represented by the quaternized protein hydrolysates.

The alkylamidoamines are usually manufactured by amidation of natural or synthetic fatty acids and fatty acid cuts with dialkylaminoamines. One compound from this group of substances that is particularly suitable according to the present invention is represented by the stearamidopropyldimethylamine available commercially under the designation TEGO AMID S 18 developed and distributed by Evonik Industries.

Also highly biodegradable are quaternary ester compounds, so-called "esterquats." Esterquats are substances that include both at least one ester function and at least one quaternary ammonium group as a structural element. Preferred esterquats are quaternized ester salts of fatty acids with triethanolamine, quaternized ester salts of fatty acids with diethanolalkylamines, and quaternized ester salts of fatty acids with 1,2-dihydroxypropyldialkylamines. Such products are marketed, for example, under the trademarks STEPANTEX polymer developed and distributed by Stepan Company, DEHYQUART polymer developed and distributed by BASF Societas Europaea, and ARMOCARE polymer developed and distributed by Akzo Nobel N.V. The products ARMOCARE VGH-70 polymer, an N,N-bis(2-palmitoyloxyethyl)dimethylammonium chloride developed and distributed by Akzo Nobel N.V., and DEHYQUART F-75 polymer, DEHYQUART C-4046 polymer, DEHYQUART L80 polymer, and DEHYQUART AU-35 polymer developed and distributed by BASF Societas Europaea are examples of such esterquats.

Cationic surfactants are included in the agents used according to the present invention preferably in quantities from 0.05 to 10 wt %, based on the total agent. Quantities from 0.1 to 5 wt % are particularly preferred.

In a preferred embodiment, nonionic, zwitterionic, and/or amphoteric surfactants, as well as mixtures thereof, may be preferred.

The agents according to the present invention may furthermore include further active agents, adjuvants, and additives, for example:
nonionic polymers such as vinylpyrrolidinone/vinyl acrylate copolymers, polyvinylpyrrolidinone, vinylpyrrolidinone/vinyl acetate copolymers, polyethylene glycols, and polysiloxanes;
silicones such as volatile or nonvolatile, straight-chain, branched, or cyclic, crosslinked or uncrosslinked polyalkylsiloxanes (such as dimethicones or cyclomethicones), polyarylsiloxanes and/or polyalkylarylsiloxanes, in particular polysiloxanes having organofunctional groups, such as substituted or unsubstituted amines (amodimethicones), carboxyl, alkoxy, and/or hydroxyl groups (dimethicone copolyols), linear polysiloxane(A)-polyoxyalkylene(B) block copolymers, grafted silicone polymers having a non-silicone-including organic backbone or having a polysiloxane backbone, such as the commercial product Abil B 8832 of the Degussa company marketed under the INCI name Bis-PEG/PPG-20/20 Dimethicone, or mixtures thereof;

structuring agents such as glucose, maleic acid, and lactic acid;

hair-conditioning compounds such as phospholipids, for example soy lecithin, egg lecithin, and kephalins, as well as silicone oils;

perfume oils, dimethylisosorbide, and cyclodextrins;

solvents and solubilizers such as ethanol, isopropanol, ethylene glycol, propylene glycol, glycerol, and diethylene glycol;

fiber-structure-improving active agents, in particular mono-, di- and oligosaccharides such as glucose, galactose, fructose, fruit sugars, and lactose;

quaternized amines such as methyl-1-alkylamidoethyl-2-alkylimidazolium methosulfate;

defoamers such as silicone;

dyes for coloring the agent;

anti-dandruff active substances such as piroctone olamine, zinc omadine and climbazol;

amino acids and oligopeptides, in particular arginine and/or serine;

animal- and/or plant-based protein hydrolysates, for example elastin, collagen, keratin, silk, and milk protein hydrolysates, or almond, rice, pea, potato, and wheat protein hydrolysates, as well as derivatives in the form of fatty acid condensation products thereof or optionally anionically or cationically modified derivatives;

vegetable oils, for example macadamia nut oil, kukui nut oil, palm oil, amaranth seed oil, peach kernel oil, avocado oil, olive oil, coconut oil, rapeseed oil, sesame oil, jojoba oil, soy oil, peanut oil, evening primrose oil, and tea tree oil;

light-protection agents, in particular derivatized benzophenones, cinnamic acid derivatives, and triazines;

substances for adjusting pH, for example usual acids, in particular edible acids, and bases;

active agents such as panthenol, pantothenic acid, pantolactone, allantoin, pyrrolidinonecarboxylic acids and salts thereof, as well as bisabolol;

polyphenols, in particular hydroxycinnamic acids, 6,7-dihydroxycumarins, hydroxybenzoic acids, catechins, tannins, leucoanthocyanidins, anthocyanidins, flavanones, flavones, and flavonols;

ceramides, preferably sphingolipids such as ceramide I, ceramide II, ceramide 1, ceramide 2, ceramide 3, ceramide 5, and ceramide 6, or pseudoceramides, such as especially N—($C_8$ to $C_{22}$ acyl)-($C_8$ to $C_{22}$ acyl)hydroxyproline;

vitamins, provitamins, and vitamin precursors, in particular those of groups A, $B_3$, $B_5$, $B_6$, C, E, F, and H;

consistency agents such as sugar esters, polyol esters, or polyolalkyl ethers;

fats and waxes such as spermaceti, beeswax, montan wax, and paraffins;

fatty acid alkanolamides;

swelling and penetration substances such as glycerol, propylene glycol monoethyl ether, carbonates, hydrogen carbonates, guanidines, ureas, and primary, secondary, and tertiary phosphates;

opacifiers such as latex, styrene/PVP copolymers and styrene/acrylamide copolymers;

luster agents such as ethylene glycol mono- and distearate as well as PEG-3 distearate;

pigments;

stabilizing agents for hydrogen peroxide and other oxidizing agents;

propellants such as propane/butane mixtures, $N_2O$, dimethyl ether, $CO_2$, and air; and antioxidants.

One skilled in the art will make a selection of these substances in accordance with the desired properties.

Coloring and lightening processes on keratin fibers usually proceed in an alkaline environment. In order to minimize stress on the keratin fibers and also on the skin, however, it is not desirable to establish too high a pH. It is therefore preferred if the pH of the ready-to-use agent is between 6 and 11, in particularly between 7 and 10.5. The pH values for purposes of the present invention are pH values that were measured at a temperature of 22° C.

Organic alkalizing agents usable according to the present invention are preferably selected from alkanolamines of primary, secondary, or tertiary amines having a $C_2$ to $C_6$ alkyl base element that carries at least one hydroxyl group. Particularly preferred alkanolamines are selected from the group: 2-aminoethan-1-ol (monoethanolamine), 2-amino-2-methyl-propan-1-ol, 2-amino-2-methylpropane-1,3-diol, and triethanolamine. It has emerged in the context of investigations related to the present invention, however, that agents further preferred according to the present invention are characterized in that they additionally include an inorganic alkalizing agent. The inorganic alkalizing agents according to the present invention are preferably selected from the group constituted from sodium hydroxide, potassium hydroxide, calcium hydroxide, barium hydroxide, sodium phosphate, potassium phosphate, sodium silicate, potassium silicate, sodium carbonate, and potassium carbonate. Sodium hydroxide and/or potassium hydroxide are very particularly preferred. The basic amino acids usable as alkalizing agents are preferably selected from the group that is constituted from L-arginine, D-arginine, D,L-arginine, L-lysine, D-lysine, D,L-lysine, particularly preferably L-arginine, D-arginine, D,L-arginine used as an alkalizing agent for purposes of the invention. Lastly, a further preferred alkalizing agent is ammonia.

With regard to further optional components, as well as the quantities of those components used, reference is made expressly to the relevant manuals known to one skilled in the art, e.g. Kh. Schrader, Grundlagen and Rezepturen der Kosmetika [Cosmetics fundamentals and formulations], 2nd ed., Hüthig Buch Verlag, Heidelberg, 1989.

The additional active agents and adjuvants are employed in the agents according to the present invention preferably in quantities respectively from 0.0001 to 10 wt %, in particular from 0.0005 to 5 wt %, based on the total weight of the utilization mixture.

A further subject of the invention is the use of an agent according to the present invention in order to color and/or lighten keratin-including fibers, in particular, human hair.

It is particularly preferred to use an agent according to the present invention to improve the color absorption of coloring agents onto keratinic fibers, and/or to improve the washing stability of colored keratinic fibers.

For utilization of the agents according to the present invention, a method for coloring and/or lightening keratinic fibers, in particular human hair, which is characterized in that an agent of the first subject of the invention, is applied onto the keratin-including fibers, left on the fibers for 5 to 60 minutes, and then rinsed out again with water or washed out with a shampoo, is particularly suitable. The contact time of the ready-to-use coloring agents is preferably 5 to 45 minutes, in particular 10 to 40 minutes, particularly preferably 15 to 35 minutes. During the contact time of the agent on the fibers, it may be advantageous to assist the lightening operation by delivering heat. Heat delivery may occur by way of an external heat source, for example warm air from a warm air blower, and also, in particular in the case of a hair lightening process on living subjects, by way of the body temperature of the subject. With the latter option, the portion to be lightened is usually covered with a hood. A contact phase at room temperature is likewise in accordance with the present invention. The temperature during the contact time is in particular between 20° C. and 40° C., in particular between 25° C. and 38° C. Once the contact time has ended, the remaining coloring preparation is rinsed out of the hair with water or a cleaning agent. Commercial shampoo, in particular, may serve as a cleaning agent. If the lightening agent possesses a highly surfactant-including carrier, it is then possible to omit the cleaning agent and perform the rinsing-out operation with water.

The agents according to the present invention may be formulated and correspondingly utilized as one-component agents or as multi-component agents, such as two-component agents or three-component agents. A separation into multi-component systems is advisable in particular when incompatibilities of the ingredients are a possibility or a risk. With such systems, the agent to be used is produced by the consumer directly before use, by mixing the components. In the case of an oxidizing coloring method, a coloring and lightening method in which the lightening cream and the oxidizing agent are initially present separately is preferred.

A further subject of the present invention is therefore a method for coloring and/or lightening keratinic fibers which is characterized in that:
- if desired, a pretreatment agent M1 is applied onto the fibers, then a coloring and/or lightening agent M2 is utilized on the fibers;
- a further agent M3 being added, if desired, to the agent M2 before utilization;
- said agent M2 is rinsed off the fibers after a time from 5 to 30 minutes; and
- after the treatment, a post-treatment agent M4 is optionally applied onto the fibers and is rinsed off again after a contact time from 2 to 25 minutes, wherein the agent M2 is an agent according to the present invention.

The statements made regarding the agents according to the present invention apply mutatis mutandis with regard to further preferred embodiments of the methods and uses according to the present invention.

The examples below are intended to explain the subject matter of the present application further without, however, limiting it in any way whatsoever.

EXEMPLIFYING EMBODIMENTS

1. Intensifying Color Absorption:

The following formulas were produced. Unless otherwise noted, the respective quantity indications are understood as percentages by weight. V1 and V2 are comparison formulas; E1 and E2 represent the corresponding formulations according to the present invention.

TABLE 1

Formulations of the Present Invention

| Raw materials | V1 | E1 | V2 | E2 |
|---|---|---|---|---|
| LANETTE D | 9.00 | 9.00 | 8.10 | 8.10 |
| LOROL TECHNISCH | 3.10 | 3.10 | 2.80 | 2.80 |
| TEXAPON NSO, 27% | 11.0 | 11.0 | 10.00 | 10.00 |

TABLE 1-continued

Formulations of the Present Invention

| Raw materials | V1 | E1 | V2 | E2 |
|---|---|---|---|---|
| Plantapon LGC | 5.55 | 5.55 | 5.00 | 5.00 |
| EUMULGIN B1 | 0.28 | 0.28 | 0.25 | 0.25 |
| Ceteareth-20 | 0.50 | 0.50 | 0.25 | 0.25 |
| Isostearic acid | 2.22 | 2.22 | 2.00 | 2.00 |
| Myristic acid 98-100 | 0.56 | 0.56 | 0.50 | 0.50 |
| Product W 37194 | 2.00 | 2.00 | 1.00 | 1.00 |
| Potassium hydroxide 50% | 1.63 | 1.63 | 1.20 | 1.20 |
| Syntran PC 5330 | — | 5.00 | — | 5.00 |
| p-Toluylenediamine, sulfate | 1.15 | 1.15 | 1.08 | 1.08 |
| 2,4,5,6-Tetraaminopyrimidine, sulfate | 1.10 | 1.10 | 1.02 | 1.02 |
| Resorcinol | 0.14 | 0.14 | 0.11 | 0.11 |
| 2-Methylresorcinol | 0.60 | 0.60 | 0.54 | 0.54 |
| 2-Amino-3-hydroxypyridine | 0.41 | 0.41 | 0.40 | 0.40 |
| 2,7-Dihydroxynaphthalene | 0.03 | 0.03 | 0.03 | 0.03 |
| 4-Amino-3-nitrophenol | 0.01 | 0.01 | — | — |
| 2-[(4-Amino-2-nitrophenyl)-amino]benzoic acid | — | — | 0.09 | 0.09 |
| Sodium sulfite, anhydrous, 96% | 0.30 | 0.30 | 0.50 | 0.50 |
| Ascorbic acid | 0.05 | 0.05 | 0.40 | 0.40 |
| Ammonium sulfate, tech. pure | 0.30 | 0.30 | 0.30 | 0.30 |
| Sodium silicate 40/42 | 0.50 | 0.50 | 0.50 | 0.50 |
| 1-Hydroxyethane-1,1-diphosphonic acid, 60% | 0.20 | 0.20 | 0.20 | 0.20 |
| Ammonia, 25% | 7.10 | 7.10 | 7.10 | 7.10 |
| Water | to 100 | to 100 | to 100 | to 100 |

The color creams V1 and E1 were mixed at a 1:1 ratio, immediately before use, with the following oxidizing agent preparation (Ox 1):

TABLE 2

Oxidizing Agent Preparation 1

| (Ox 1) raw material | Quantity |
|---|---|
| EDTA, disodium salt | 0.15 |
| Disodium pyrophosphate | 0.30 |
| Sodium benzoate | 0.04 |
| EMULGADE F | 2.10 |
| Hydrogen peroxide, 50% | 12.00 |
| Water | to 100 |

The color creams V2 and E2 were mixed at a 1:1 ratio, immediately before use, with the following oxidizing agent preparation (Ox 2):

TABLE 3

Oxidizing Agent Preparation 2

| (Ox 2) raw material | Quantity |
|---|---|
| Sodium hydroxide, 45%, tech. | 0.73 |
| Dipicolinic acid | 0.10 |
| Disodium pyrophosphate | 0.03 |
| 1-Hydroxyethane-1,1-diphosphonic acid, 60% | 1.50 |
| TEXAPON NSO, 27% | 2.00 |
| Dow Corning DB 110 A (nonionic silicone emulsion) | 0.07 |
| ACULYN 33A | 12.00 |
| Hydrogen peroxide, 50% | 12.00 |
| Water | to 100 |

List of raw materials used:
ACULYN 33A acrylates copolymer developed and distributed by The Dow Chemical Company: approx. 28% solids in water;
LANETTE D cetearyl alcohol developed and distributed by Cognis GmbH: $C_{16-18}$ fatty alcohol;

LOROL TECHNISCH coconut alcohol developed and distributed by Cognis GmbH: $C_{12-18}$ fatty alcohol;

TEXAPON NSO sodium laureth sulfate developed and distributed by Cognis GmbH: Lauryl ether sulfate, sodium salt (approx. 27.5% active substance;

PLANTAPON LGC lauryl glucose carboxylate and lauryl glucoside developed and distributed by Cognis GmbH: approx. 28-34% active substance in water;

EUMULGIN B1 ceteareth-12 developed and distributed by Cognis GmbH: Cetyl stearyl alcohol with approx. 12 EO units;

EMULGADE F cetearyl alcohol, PEG-40 castor oil, and sodium cetearyl sulfate developed and distributed by Cognis GmbH;

Ceteareth-20 polyoxyethylene ethers with fatty acid alcohols, and C16-18, and ethoxylated (20 EO);

Product W 37194 acrylamidopropyltrimonium chloride/acrylates copolymer: 1-propanaminium, N,N,N-trimethyl-3-[(1-oxo-2-propenyl)amino]chloride, polymer with sodium 2-propenoate;

SYNTRAN PC 5330 polyquaternium-91 (14 wt %) and polyacrylate-15 (4 wt %) developed and distributed by the Interpolymer Corporation Before the coloring process, hair strands (Euro Natural hair, white) were measured colorimetrically using a Spectraflash 450 colorimeter developed and distributed by Datacolor, AG. The ready-to-use color formulations produced as described above were then placed onto the hair strands and left there for 30 minutes at room temperature. The hair strands were then thoroughly rinsed out and dried in a stream of air. After coloring and drying, the hair strands were measured colorimetrically again. The color distance (ΔE) between uncolored and colored strands was calculated using the formula below:

$$\Delta E = \sqrt{(Lv-Ln)^2+(av-an)^2+(bv-bn)^2} \quad \text{Eq. 1}$$

where Lv, av, and bv represent colorimetric values before coloring, and Ln, an, and bn represent colorimetric values after coloring.

TABLE 4

Colorimetrically Measured Values

| Determining color absorption capability | | L | a | b | ΔE |
|---|---|---|---|---|---|
| Euro Natural hair, white | before coloring | 70.50 | 2.55 | 21.11 | |
| colored with V1 | after coloring | 21.92 | 12.29 | 6.97 | 51.5 |
| colored with E1 | after coloring | 19.98 | 12.39 | 6.60 | 53.5 |
| colored with V2 | after coloring | 20.82 | 11.62 | 5.02 | 53.0 |
| colored with E2 | after coloring | 18.89 | 9.93 | 4.07 | 54.9 |

The larger the color distance between uncolored strands and colored strands, the greater the color absorption resulting from the coloring. With the use of formulations E1 and E2 according to the present invention, an appreciably more intense color result was obtained in each case as compared with the corresponding comparison formulation.

2. Improving Washing Fastness:

In order to determine values for washing fastness or color retention, the hair strands colored with formulations V2 and E2 under item 1 were placed in an ultrasonic bath and subjected to 6, 12, 18, and 24 hair washes according to a standardized method. After each 6 hair washes the strands were removed from the ultrasonic bath, dried, and measured colorimetrically.

The colorimetric data were thus determined directly after coloring of the hair strands (0 HW), and after 6, 12, 18, and 24 hair washes.

The respective color distance (ΔE value) between the unwashed strands and those washed in defined fashion was calculated using the formula below:

$$\Delta E = \sqrt{(Lv-Ln)^2+(av-an)^2+(bv-bn)^2} \quad \text{Eq. 2}$$

where $L_0$, $a_0$, and $b_0$ are colorimetric values after 0 hair washes, and $L_x$, $a_x$, and $b_x$ are colorimetric values after 6, 12, 18, and 24 hair washes.

TABLE 5

Determined Washing Fastness Values

| Determining washing fastness values | Hair washes | L | a | b | ΔE |
|---|---|---|---|---|---|
| V2 | 0 | 20.82 | 11.62 | 5.02 | |
| | 6 | 21.97 | 14.62 | 7.39 | 4.0 |
| | 12 | 21.75 | 14.35 | 7.08 | 3.5 |
| | 18 | 21.96 | 14.35 | 6.90 | 3.5 |
| | 24 | 23.40 | 15.70 | 8.96 | 6.2 |
| E2 | 0 | 18.89 | 9.93 | 4.07 | |
| | 6 | 19.43 | 11.95 | 5.50 | 2.5 |
| | 12 | 19.44 | 12.51 | 5.92 | 3.2 |
| | 18 | 19.44 | 12.65 | 6.08 | 3.4 |
| | 24 | 19.88 | 13.11 | 6.56 | 4.2 |

The greater the color distance (ΔE value) between unwashed and washed strands, the poorer the washing fastness. A comparison of the strands colored with formulas V2 and E2 shows that the strands colored with formula E2 according to the present invention exhibited, in all washing cycles, a smaller color distance and thus better washing fastness.

What is claimed is:

1. An agent for coloring keratinic fibers included in a cosmetic carrier, the agent comprising:
at least one cationic acrylic acid ester copolymer including at least one structural unit of the general formula (I), at least one structural unit of the general formula (II), and at least one structural unit of the general formula (III),

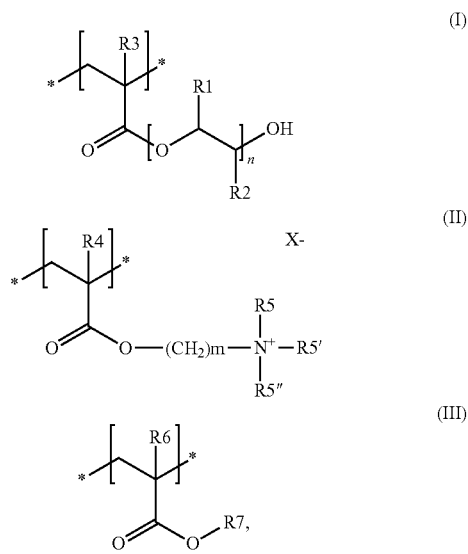

in which:
R1, R2, R3, R4, and R6 mutually independently denote a hydrogen atom or a $C_1$ to $C_6$ alkyl group,
R5, R5', R5" mutually independently denote a $C_1$ to $C_{20}$ alkyl group, a $C_2$ to $C_6$ alkenyl group, or a $C_2$ to $C_6$ hydroxyalkyl group, R7 denotes a $C_1$ to $C_6$ alkyl group, a $C_2$ to $C_6$ hydroxyalkyl group, or a $C_2$ to $C_6$ polyhydroxyalkyl group, n denotes an integer from 1 to 50,000, m denotes an integer from 2 to 6, and $X^-$ denotes a physiologically acceptable anion, and at least one color-changing compound.

2. The agent of claim 1, wherein the residues R1, R2, and R3 denote a hydrogen atom, the residues R4, R5, R5', R5", and R6 denote a methyl group, the residue R7 denotes a $C_2$ to $C_6$ hydroxyalkyl group, and m is equal to 2 or 3.

3. The agent of claim 1, wherein the agent comprises, as the at least one cationic acrylic acid ester copolymer from 0.001 to 25 wt %.

4. The agent of claim 1, wherein the agent comprises, as the at least one color-changing compound, at least one oxidation dye precursor, at least one substantive dye, or combinations thereof, respectively in a quantity from 0.001 to 12 wt % based on the agent.

5. The agent of claim 1, in which the at least one color-changing compound is one of the following developer/coupler combinations: p-toluoylenediamine/resorcinol; p-toluoylenediamine/2-methylresorcinol; p-toluoylenediamine/2-amino-3-hydroxypyridine; p-toluoylenediamine/2,7-dihydroxynaphthalene; p-toluoylenediamine/3-aminophenol; p-toluoylenediamine/1-naphthol; p-toluoylenediamine/1,5-dihydroxynaphthalene; p-toluoylenediamine/5-amino-2-methylphenol; p-toluoylenediamine/2-(2,4-diaminophenoxy)ethanol; p-toluoylenediamine/3-amino-2-chloro-6-methylphenol; p-toluoylenediamine/2,6-dihydroxy-3,4-dimethylpyridine; p-toluoylenediamine/3-amino-2-methylamino-6-methoxypyridine; p-toluoylenediamine/1,3-bis(2,4-diaminophenyl)propane; 2,4,5,6-tetraminopyrimidine/resorcinol; 2,4,5,6-tetraminopyrimidine/2-methylresorcinol; 2,4,5,6-tetraminopyrimidine/2-amino-3-hydroxypyridine; 2,4,5,6-tetraminopyrimidine/2,7-dihydroxynaphthalene; 4,5-diamino-1-(2-hydroxyethyl)pyrazole/resorcinol; 4,5-diamino-1-(2-hydroxyethyl)pyrazole/2-methylresorcinol; 4,5-diamino-1-(2-hydroxyethyl)pyrazole/2-amino-3-hydroxypyridine; 4,5-diamino-1-(2-hydroxyethyl)pyrazole/2,7-dihydroxynaphthalene; p-aminophenol/resorcinol; p-aminophenol/2-methylresorcinol; p-aminophenol/2-amino-3-hydroxypyridine; p-aminophenol/2,7-dihydroxynaphthalene; p-aminophenol/3-aminophenol; p-aminophenol/1-naphthol; p-aminophenol/1,5-dihydroxynaphthalene; p-aminophenol/5-amino-2-methylphenol; p-aminophenol/2-(2,4-diaminophenoxy)ethanol; p-aminophenol/3-amino-2-chloro-6-methylphenol; p-aminophenol/2,6-dihydroxy-3,4-dimethylpyridine; p-aminophenol/3-amino-2-methylamino-6-methoxypyridine; or p-aminophenol/1,3-bis(2,4-diaminophenyl)propane.

6. The agent of claim 1, wherein the at least one color-changing compound is selected from the group consisting of one of the following combinations of two developers and one coupler: p-toluoylenediamine/2,4,5,6-tetraminopyrimidine/resorcinol; p-toluoylenediamine/2,4,5,6-tetraminopyrimidine/2-methylresorcinol; p-toluoylenediamine/2,4,5,6-tetraminopyrimidine/2-amino-3-hydroxypyridine; and p-toluoylenediamine/2,4,5,6-tetraminopyrimidine/2,7-dihydroxynaphthalene.

7. The agent of claim 1, wherein the at least one color-changing compound is selected from the group consisting of nonionic substantive: HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9,1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

8. The agent of claim 1, wherein the at least one color-changing compound comprises 4-amino-3-nitrophenol as a substantive dye, alone or in combination with additional color-changing compounds.

9. The agent of claim 1, wherein the at least one color-changing compound comprises:

a substantive dye; and an oxidation dye precursor of the developer type, an oxidation dye precursor of the coupler type, or combinations thereof.

10. The agent of claim 1, wherein the at least one color-changing compound comprises at least one oxidizing agent selected from hydrogen peroxide or solid addition products thereof with organic or inorganic compounds, wherein the at least one oxidizing agent is in a quantity from 0.001 to 12 wt % based on the agent.

11. The agent of claim 1, further comprising, based on the agent, 0.01 to 30 wt % of a bleaching power intensifier selected from ammonium peroxodisulfate, potassium peroxodisulfate, sodium peroxodisulfate, potassium hydrogen peroxomonosulfate, potassium peroxodiphosphate, magnesium peroxide, or barium peroxide.

12. The agent of claim 1, further comprising, based on the agent, 0.001 to 20 wt % of at least one anionic acrylic acid polymer, at least one anionic acrylic acid copolymer, or combinations thereof.

13. The agent of claim 12, wherein the anionic acrylic acid copolymer is polyacrylate-15.

14. The agent of claim 1, wherein the agent is applied to keratinic fibers.

15. A method for coloring keratinic fibers, comprising:

applying a pretreatment agent to the keratinic fibers;

applying the coloring agent to the keratinic fibers;

rinsing said coloring agent off the keratinic fibers after a time period, and optionally applying a post-treatment agent M4 onto the fibers; and rinsing the post-treatment agent M4 off after a contact time from 2 to 25 minutes, wherein the coloring agent comprises:

at least one cationic acrylic acid ester copolymer including at least one structural unit of the general formula (I), at least one structural unit of the general formula (II), and at least one structural unit of the general formula (III),

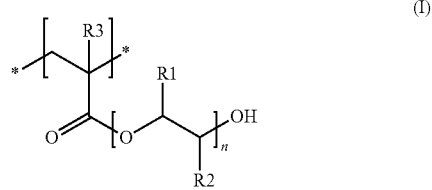

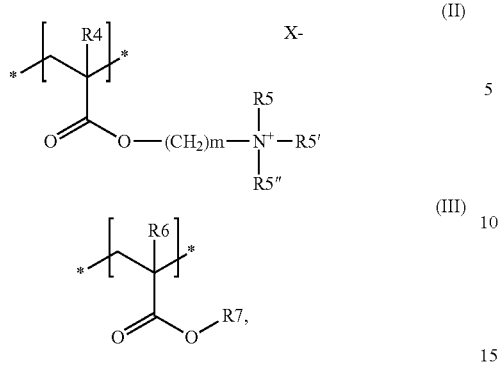

wherein
- R1, R2, R3, R4, and R6 mutually independently denote a hydrogen atom or a $C_1$ to $C_6$ alkyl group,
- R5, R5', R5" mutually independently denote a $C_1$ to $C_{20}$ alkyl group, a $C_2$ to $C_6$ alkenyl group, or a $C_2$ to $C_6$ hydroxyalkyl group,
- R7 denotes a $C_1$ to $C_6$ alkyl group, a $C_2$ to $C_6$ hydroxyalkyl group, or a $C_2$ to $C_6$ polyhydroxyalkyl group,
- n denotes an integer from 1 to 50,000,
- m denotes an integer from 2 to 6, and
- $X^-$ denotes a physiologically acceptable anion, and at least one color-changing compound.

16. The method of claim 15, further comprising adding a second agent to the coloring agent before applying the coloring agent to the keratinic fibers.

17. The method of claim 15, wherein the time period is between 5 and 30 minutes.

* * * * *